(12) United States Patent
Fumoto

(10) Patent No.: US 7,612,225 B2
(45) Date of Patent: Nov. 3, 2009

(54) CRYSTAL OF TRITERPENE DERIVATIVE

(75) Inventor: Masataka Fumoto, Amagasaki (JP)

(73) Assignee: Shionogi & Co., Ltd., Osaka (JP)

( * ) Notice: Subject to any disclaimer, the term of this patent is extended or adjusted under 35 U.S.C. 154(b) by 333 days.

(21) Appl. No.: 10/592,540

(22) PCT Filed: Mar. 24, 2005

(86) PCT No.: PCT/JP2005/005317

§ 371 (c)(1),
(2), (4) Date: May 31, 2007

(87) PCT Pub. No.: WO2005/090285

PCT Pub. Date: Sep. 29, 2005

(65) Prior Publication Data

US 2007/0282126 A1 Dec. 6, 2007

(30) Foreign Application Priority Data

Mar. 24, 2004 (JP) ............................. 2004-085884

(51) Int. Cl.
*C07C 229/00* (2006.01)
(52) U.S. Cl. .................... 560/43; 562/403; 562/441
(58) Field of Classification Search .................. 560/43; 562/403, 441
See application file for complete search history.

(56) References Cited

U.S. PATENT DOCUMENTS 5,463,107 A    10/1995  Konoike et al.
5,587,505 A *  12/1996  Konoike et al. ............. 558/272

FOREIGN PATENT DOCUMENTS

| EP | 1 407 775 A1 | 4/2004 |
| EP | 1 489 091 A1 | 12/2004 |
| EP | 1489091 A1 * | 12/2004 |
| JP | 07-316188 | 12/1995 |
| WO | WO 97/27314 | 7/1997 |
| WO | WO 98/18497 | 5/1998 |
| WO | WO 03/080643 | 10/2003 |

OTHER PUBLICATIONS

English language translation of International Preliminary Report on Patentability issued in PCT/JP2005/005317, Oct. 26, 2006, 5 pages.
T. Konoike, et al., "Practical Large-Scale Synthesis of Endothelin Receptor Angtagonist S-0139," Organic Process Research & Development, vol. 3, pp. 347-351 (1999).

* cited by examiner

*Primary Examiner*—Peter G O'Sullivan
*Assistant Examiner*—Sudhakar Katakam
(74) *Attorney, Agent, or Firm*—Finnegan, Henderson, Farabow, Garrett & Dunner, L.L.P.

(57) ABSTRACT

Disclosed herein are a novel crystal of a novel triterpene derivative, a method for producing the crystals, and a pharmaceutical preparation obtained by using the crystals.

The novel crystal is a crystal of a compound (I) of the formula (I):

[Chemical Formula 1]

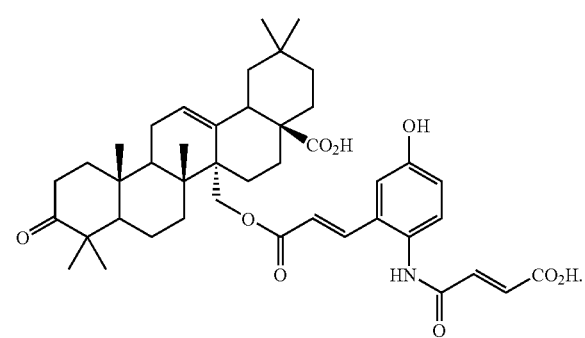

3 Claims, No Drawings ably
CRYSTAL OF TRITERPENE DERIVATIVE

TECHNICAL FIELD

The present invention relates to a novel crystal of a triterpene derivative, a method for producing the crystals, and a pharmaceutical preparation obtained by using the crystals.

BACKGROUND ART

It is known that a compound of the formula:

[Chemical Formula 1]

(hereinafter, the compound will be referred to as "Compound A") is an endothelin receptor antagonist, and is useful for treating various circulatory system diseases such as hypertension, ischemic disorders, cerebral circulatory disorders, renal disorders, circulatory insufficiency of various organs, asthma, stroke, cerebral infarction, cerebral edema and the like (see Patent Literatures 1 and 2).

Further, a free compound of Compound A of the formula (I):

[Chemical Formula 2]

(hereinafter, the compound will be referred to as "Compound (I)") has been already isolated as pale yellow needle crystals by using ethyl acetate as a solvent for recrystallization (see Non-patent Literature 1).

Patent Literature 3 discloses a pharmaceutical preparation obtained by freeze-drying a solution or suspension prepared by adding a basic substance to Compound A or Compound (I).

Patent Literature 4 discloses a process for isolating Compound (I) as crystals from a solution prepared by adding an organic solvent and water to a reaction mixture containing Compound (I). However, in Patent Literature 4, only ethyl acetate is mentioned as a specific example of the organic solvent, and there is no reference made to a form II crystal of Compound (I) of the present invention.

[Non-Patent Literature 1] Organic Process Research & Development, 1999, vol. 3, pp.347-351

[Patent Literature 1] Japanese Patent Laid-open No. H7-53484

[Patent Literature 2] Japanese Patent Laid-open No. H7-316188

[Patent Literature 3] WO 03/007967

[Patent Literature 4] WO 03/080643

DISCLOSURE OF INVENTION

Problems to be Solved by the Invention

In general, drug substances for use in pharmaceutical preparations are required to have very high quality, and therefore it is necessary to prevent the quality of such drug substances from being deteriorated with the passage of time as much as possible. It is therefore an object of the present invention is to provide a novel crystal of Compound (I) having excellent storage stability.

Means to Solve the Problem

The present invention provides the followings:

(1) a crystal of a compound of the formula (I):

[Chemical Formula 3]

which exhibits a powder X-ray diffraction pattern having main peaks at diffraction angles (2θ) of 6.0, 6.5, 12.6, 13.6, and 15.4 (degree) (hereinafter, referred to as a "form II crystal");

(2) a method for producing the crystals as described in the above (1) comprising suspending or dissolving crystals of a compound of the formula (I):

[Chemical Formula 4]

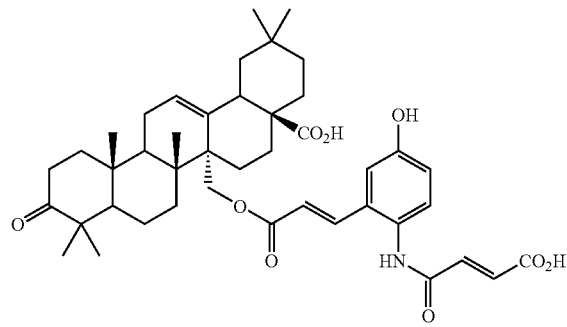
(I)

which exhibit a powder X-ray diffraction pattern having main peaks at diffraction angles (2θ) of 4.6, 7.7, 12.7, 16.7, 19.1 and 21.1 (degree) in acetonitrile to change their crystal form; and (3) a method for producing a pharmaceutical preparation comprising mixing the crystals as described in the above (1), a solvent and sodium hydroxide, and drying the mixture.

Further, the present invention provides the followings:

(4) a method for producing the crystals as described in the above (1) comprising:

(step 1) a step of adding ethyl acetate to a solution containing a compound of the formula (I):

[Chemical Formula 5]

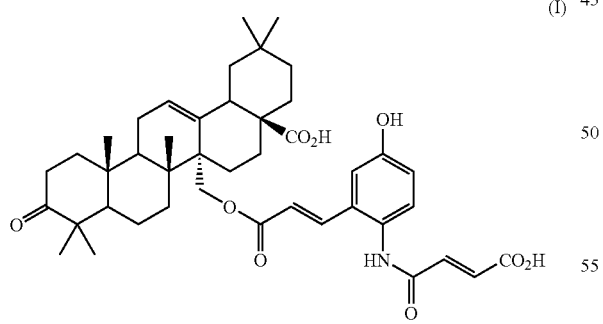
(I)

to obtain crystals, and (step 2) a step of suspending or dissolving the obtained crystals in acetonitrile to change their crystal form;

(5) a method for producing the crystals as described in the above (1), wherein the compound of the formula (I) according to the above (4) is obtained by treating a compound of the formula (II):

[Chemical Formula 6]

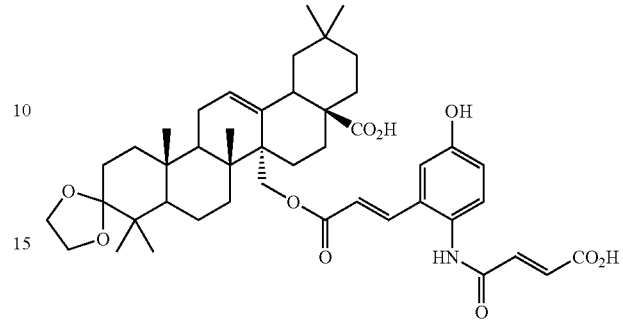
(II)

with an acid;

(6) a method for producing the crystals as described in the above (1), wherein the compound of the formula (II) according to the above (5) is obtained by reacting a compound of the formula (III):

[Chemical Formula 7]

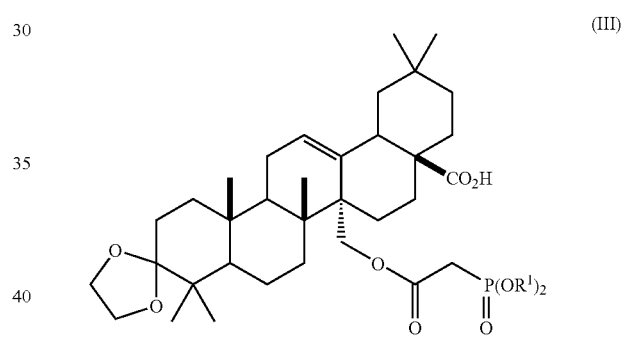
(III)

wherein $R^1$ represents lower alkyl, with a compound of the formula (IV):

[Chemical Formula 8]

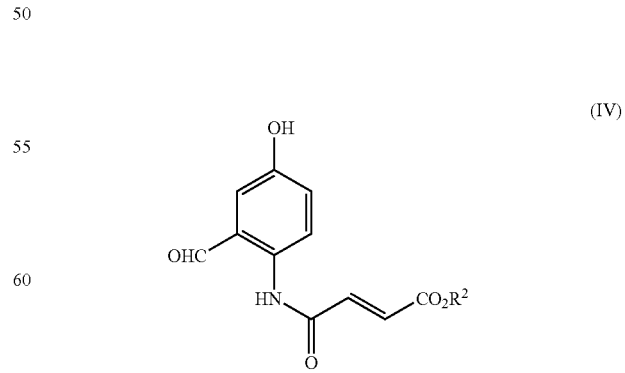
(IV)

wherein $R^2$ represents hydrogen or lower alkyl, in the presence of a base, an organic solvent and water; and (7) use of the crystals as described in the above (1) for producing a therapeutic and/or prophylactic pharmaceutical preparation for acute cerebrovascular disease.

EFFECT OF THE INVENTION

The form II crystals of Compound (I) of the present invention are superior to other form of crystals in storage stability, thereby suppressing a reduction in the amount of Compound (I) contained in a drug substance during storage. This makes it possible to maintain the quality of the drug substance.

BEST NODE FOR CARRYING OUT THE INVENTION

A method for producing the above-mentioned form II crystals is not particularly limited, but such form II crystals are preferably produced in accordance with the following method.

(Step I: Method A)

The above-mentioned Compound (II) disclosed in, for example, Non-patent Literature 1 is dissolved or suspended in an appropriate organic solvent, and is then treated with an acid to obtain Compound (I).

Examples of the organic solvent include, but are not limited to, N,N-dimethylformamide, diethyl ether, tetrahydrofuran, N,N-dimethylacetamide, and ethylene glycol dimethyl ether.

The acid is not particularly limited as long as it can deprotect an ethylenedioxy moiety of Compound (II). Examples of such an acid include hydrochloric acid, hydrobromic acid, sulfuric acid, nitric acid, phosphoric acid, p-toluenesulfonic acid, methanesulfonic acid, formic acid, trifluoroacetic acid, maleic acid, and oxalic acid. Hydrochloric acid is preferably used. The amount of the acid to be used is in the range of about 0.1 to 15.0 mole equivalents, preferably in the range of about 1.0 to 3.0 mole equivalents, per mole equivalent of Compound (II).

The temperature for acid treatment is usually in the range of about 0 to 80° C., preferably in the range of about 40 to 50° C.

The time for acid treatment is usually in the range of 0.1 to 20 hours, preferably in the range of about 30 minutes to 2 hours.

It is not necessary to isolate the thus obtained Compound (I), and the solution containing Compound (I) can be used as it is in Step 2.

(Step 1: Method B)

Alternatively, Compound (I) may be produced by reacting Compound (III) with Compound (IV). Specifically, Compound (I) is produced in accordance with a method disclosed in Patent Literature 4.

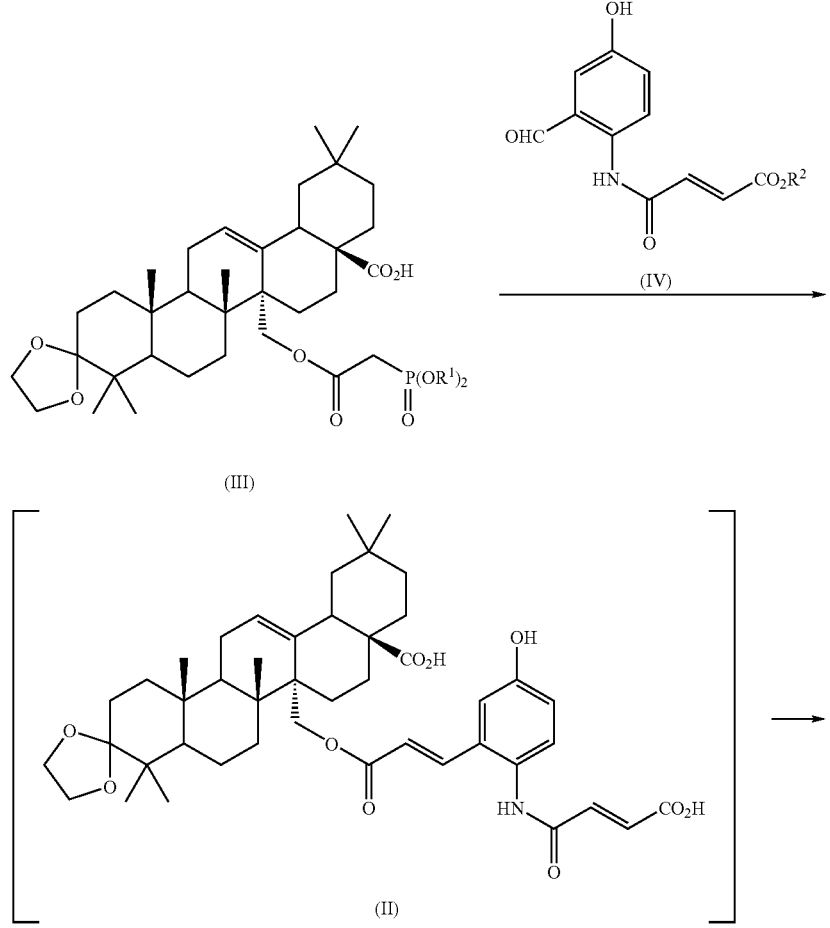

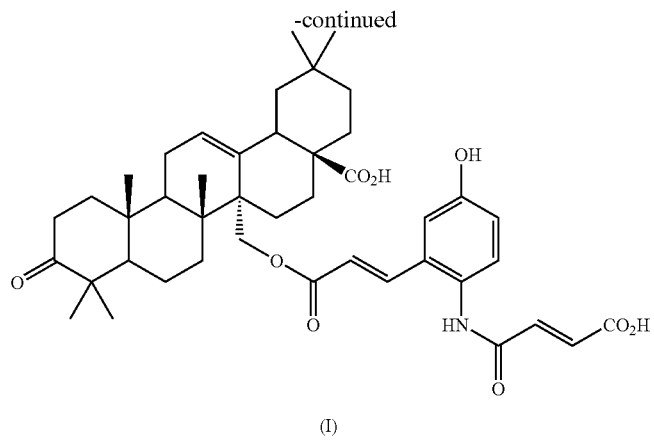

(I)

wherein $R^1$ represents lower alkyl, and $R^2$ represents hydrogen or lower alkyl.

Compound (III) is reacted with Compound (IV) in the presence of a base, an organic solvent, and water to obtain a solution containing Compound (II). It is not necessary to isolate Compound (II) from the solution, and an acid is added to the solution containing Compound (II) to produce Compound (I).

Examples of the base include lithium hydroxide, sodium hydroxide, potassium hydroxide, and the like. Lithium hydroxide is preferably used. The amount of the base to be used is in the range of about 3.0 to 10.0 mole equivalents, preferably in the range of about 2.0 to 5.0 mole equivalents, relative to Compound (I).

Examples of the organic solvent include N,N-dimethylformamide, diethyl ether, tetrahydrofuran, N,N-dimethylacetamide, ethylene glycol dimethyl ether, and the like. N,N-dimethylformamide is preferably used.

The amount of water to be added is not particularly limited. For example, the base may be used as a 0.1% (w/w) to 30% (w/w), preferably 1% (w/w) to 10% (w/w) aqueous solution of the base for the reaction.

The reaction temperature is usually in the range of about −40 to 60° C., preferably in the range of about −10 to 0° C. The reaction time is usually in the range of about 15 minutes to 10 hours, preferably in the range of about 30 minutes to 4 hours.

Examples of the acid to be added, the amount of the acid to be added, the temperature, and the time are the same as those described with reference to the step 1 by Method A.

It is not necessary to isolate Compound (I) from the solution, and the solution containing Compound (I) can be used as it is in the next step 2.

Examples of lower alkyl represented by $R^1$ or $R^2$ include straight or branched alkyls having 1 to 8 carbon atoms, such as methyl, ethyl, n-propyl, isopropyl, n-butyl, isobutyl, sec-butyl, tert-butyl, n-pentyl, isopentyl, neopentyl, hexyl, isohexyl v , n-heptyl, isoheptyl, n-octyl, and isooctyl. $R^1$ is preferably methyl or ethyl, particularly preferably ethyl, and $R^2$ is preferably methyl.

The phrase "a solution containing a compound of the formula (I)" in the step 1 in the above (4) includes a reaction mixture obtained in the step 1 by Method A or in the step 1 by Method B, and more specifically refers to a "solution of N,N-dimethylformamide, diethyl ether, tetrahydrofuran, N,N-dimethylacetamide, or ethylene glycol dimethyl ether containing a compound of the formula (I)", preferably a "solution of N,N-dimethylformamide containing a compound of the formula (I)".

(Step 2)

The solution containing Compound (I) is cooled to about room temperature, and then an appropriate amount of ethyl acetate is added to the solution. If necessary, an appropriate amount of water is also added to the solution. At this time, the pH of the solution may be adjusted to about 5 to 6 with a base.

The amount of ethyl acetate and the amount of water are not particularly limited, but is each preferably 5 to 20 mL per gram of Compound (I).

The base to be used is not particularly limited as long as it is generally used. Examples of such a base include sodium hydroxide, potassium hydroxide, and lithium hydroxide.

Then, moisture is removed from an organic layer by, for example, vacuum concentration, and crystallization is carried out at about 40 to 80° C., preferably about 65 to 75° C.

If necessary, acetonitrile may be further added thereto. In this case, the resultant mixture is cooled to about −10 to 0° C., and is then stirred for about 30 minutes to 2 hours to precipitate crystals. By doing so, it is possible to obtain crystals that can be easily treated in the next step.

If the crystals obtained in this step are sufficiently dried, thus obtained dry crystals are the same as pale yellow needle crystals defined as Compound 7 in Non-patent Literature 1 (form I dry crystals). Such dry crystals may be used in the next step, but the crystals containing the solvent (form I wet crystals) may be used as they are in the next step. Here, the phrase "the crystals containing the solvent" includes both crystals of solvate and crystals to which the solvent is adhered.

(Step 3)

The form I crystals obtained in the step 2 are suspended or dissolved in an appropriate amount of acetonitrile, and are then treated at room temperature to about 80° C., preferably about 40 to 50° C. for about 15 minutes to 10 hours, preferably about 30 minutes to 2 hours to change their crystal form.

The amount of acetonitrile to be used is not particularly limited, but is preferably in the range of 10 to 50 mole equivalents per mole equivalent of the form I dry crystals or the form I wet crystals.

Then, the suspension or solution is cooled to about −10° C. to close to room temperature, and is stirred for about 15 minutes to 5 hours, preferably about 15 minutes to 1 hour to obtain crystals. It is possible to improve the purity of the crystals by washing the obtained crystals with an appropriate amount of acetonitrile. The thus obtained crystals are sufficiently dried to remove the solvent. In this way, form II crystals are obtained.

According to the method of the present invention, crystallization is carried out to obtain form I crystals of Compound (I), and crystallization is further carried out to obtain form II crystals of Compound (I). Therefore., the thus obtained crystals are highly-purified crystals.

When the form II crystals are analyzed by powder X-ray diffraction, the diffraction pattern thereof has main peaks at diffraction angles (2θ) of 6.0, 6.5, 12.6, 13.6, and 15.4 (degree).

These powder X-ray diffraction values indicate representative peaks selected from the X-ray diffraction peaks of the crystals, and therefore the structure of the crystals is not necessarily limited only by these values. That is, the powder X-ray diffraction pattern of the crystals of the present invention may have other peaks in addition to these peaks. In general, when crystals are analyzed by X-ray diffraction, measurement errors may occur in peaks to some extent depending on a measuring instrument, measuring conditions, or the presence or absence of a solvent adhered to the crystals. Therefore, any crystals characterized by having X-ray diffraction patterns substantially similar to the above described X-ray diffraction pattern are all included in the present invention.

As is clear from the experimental results described later, the form II crystals are superior in storage stability to the form I crystals, and are therefore prevented from being deteriorated in quality during storage. The form I crystals needed to be kept cold when stored for a long period of time, whereas the form II crystals of the present invention do not need to be kept cold when stored for a long period of time, which is advantageous in facilitating storage and transport.

In addition, the form II crystals have an improved stability against light. For example, in the case that the form I crystals are stored under light, the total amount of related substances of Compound (I) is increased, whereas in the case of the form II crystals, the total amount of related substances of Compound (I) is hardly changed.

The present invention also provides a pharmaceutical preparation produced using the form II crystals and use of the form II crystals for producing a pharmaceutical preparation. Here, the pharmaceutical preparation may be one containing Compound (I) as an active ingredient, and is preferably one containing Compound A, i.e., a sodium salt of Compound (I), as a pharmaceutically active ingredient.

Examples of a dosage form of a pharmaceutical preparation include tablets, granules, capsules, and injections. Injections are preferably used.

An injectable pharmaceutical preparation containing Compound A, i.e., a sodium salt of Compound (I), as an active ingredient, can be produced by a method disclosed in Patent Literature 3. In this case, conversion of Compound (I) into its sodium salt and production of a pharmaceutical preparation are carried out at the same time using the form II crystals of the present invention.

Specifically, a solvent and sodium hydroxide are mixed with the form II crystals of the present invention. Then sodium hydroxide is further added to adjust the pH of the mixture to 8.5 or higher, preferably about 9.5 to prepare a solution. The amount of sodium hydroxide to be added is in the range of 5 to 20 mg, preferably in the range of 10 to 20 mg, more preferably in the range of 12 to 18 mg, per 100 mg of the form II crystals.

Examples of the solvent include water, infusions, buffers, injection solvents, and the like. Injection solvents or infusions are preferably used.

The solution may further contain sugar (e.g., glucose, maltose, lactose, sucrose, fructose mannitol, preferably mannitol) or an amino acid (preferably a neutral amino acid, more preferably glycine or alanine, and most preferably alanine). The amount of sugar or an amino acid to be added is preferably in the range of 25% (w/w) or higher, more preferably in the range of 40 to 60% (w/w), and most preferably 50% (w/w) of Compound A.

If necessary, the solvent is further added to the solution to adjust the concentration of the solution to an appropriate value. Then, the solution is sterilized by, for example, aseptic filtration to obtain a sterile solution. The thus obtained sterile solution is dried by freeze-drying, spray-drying, or vacuum drying to obtain Compound A-containing preparation to be dissolved for use as an injection before use.

In a case where the sterile solution is spray-dried, a sterilized drying device (e.g., a spray drier, a fluidized-bed granulator) is used and thus obtained dry powder is packed in sterilized vials. The dry powder is dissolved for use as an injection before use.

When the sterile solution is spray-dried, there is a case where a resultant dry powder is electrically charged, and is therefore adhered to devices and containers, thereby significantly impairing operability. In order to suppress electrification of the dry powder to improve operability, polyethylene glycol may be added to the solution in advance.

Examples of such polyethylene glycol include polyethylene glycol 400, polyethylene glycol 600, polyethylene glycol 4000, and the mixture of two or more selected from them. PEG 4000 is preferably used. The lower limit of the amount of polyethylene glycol to be added is 0.01 mg, preferably 0.03 mg, per milligram of the form II crystals, and the upper limit of the amount of polyethylene glycol to be added is 0.5 mg, preferably 0.4 mg, more preferably 0.2 mg, per milligram of the form II crystals.

Hereinbelow, Example and Experimental Examples will be described, and they are not intended to be limiting the invention.

The conditions for X-ray diffraction analysis are as follows:

CuKα ray: λ=1.54 Å
Tube voltage: 40 kV
Tube current: 40 mA
Scanning speed: 2.000°/min
Sampling width: 0.020°

EXAMPLE 1

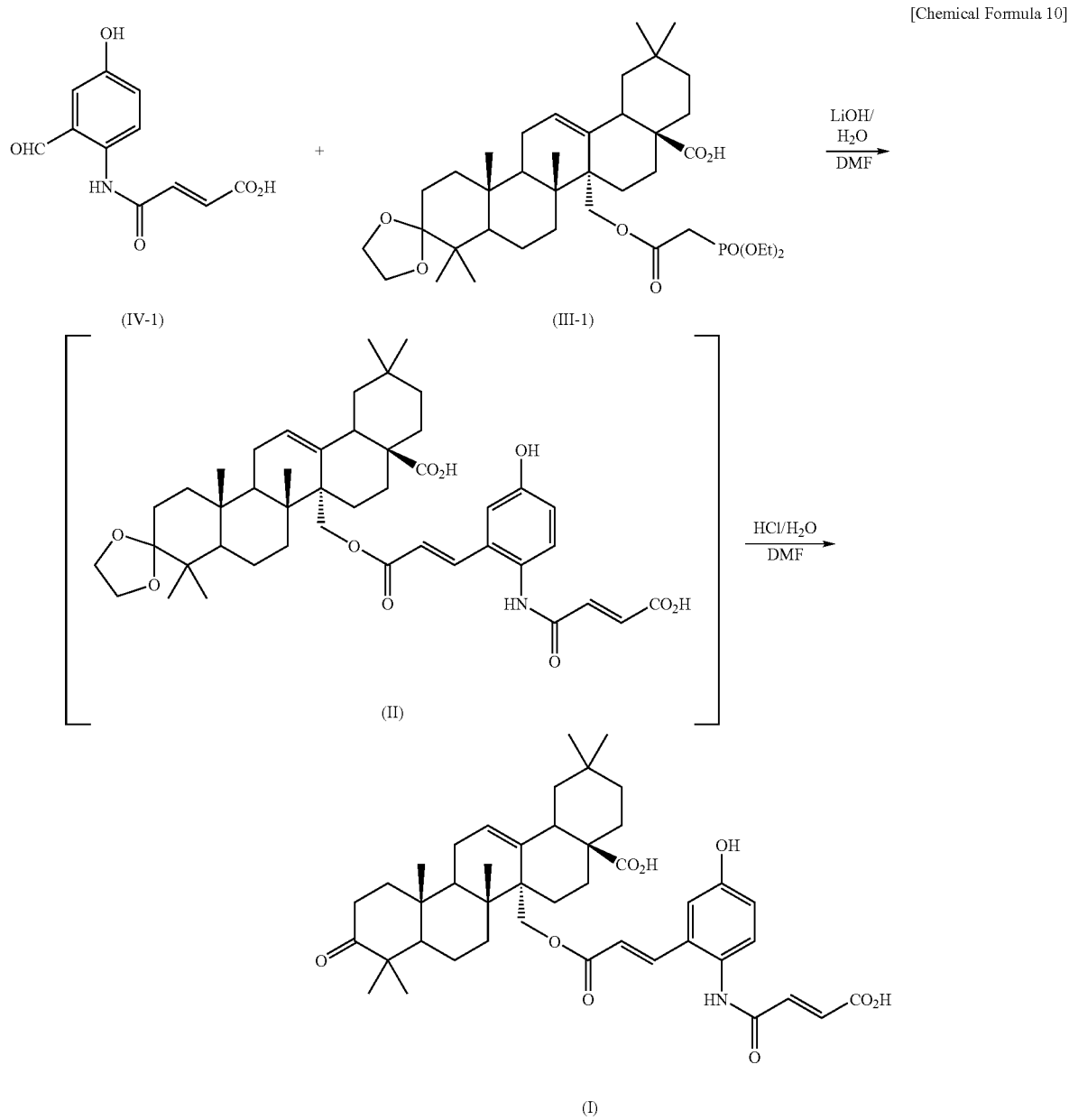

wherein Et represents ethyl, and DMF represents N,N-dimethylformamide.

Compound (III-1) (9.3 g) and Compound (IV-1) (4.0 g) were suspended in N,N-dimethylformamide (65 mL), and the resultant suspension was cooled to −5° C. or less. Into the suspension, a 5.6% aqueous solution of lithium hydroxide (28.8 g) was dropped, and the resultant mixture was reacted for 3.5 hours to obtain a solution containing Compound (II) in N,N-dimethylformamide. Then, the solution was heated to 5° C., 35% hydrochloric acid (9.1 g) was added thereto, and the resultant mixture was stirred at 45° C. for 1.5. hours. After the completion of the reaction, the reaction mixture was cooled to room temperature, and then ethyl acetate (105 mL) and water (93 g) were added to the reaction mixture. The pH of the reaction mixture was adjusted to about 5.5 with a 10% aqueous solution of sodium hydroxide, and an organic layer was separated. An aqueous layer was subjected to extraction with ethyl acetate, and then all of the organic layers were combined after washed with water. The combined solution was concentrated under a reduced pressure to remove moisture, and crystallization was carried out at 70° C. After acetonitrile (51 mL) was added thereto, the resultant mixture was gradually cooled to room temperature, further cooled to 0C, and stirred for 1 hour. A precipitated yellow solid was collected by filtration, and was then washed with acetonitrile to obtain 15.8 g of form I crystals (wet crystals) of Compound (I). Then, 15.5 g of the thus obtained form I crystals (wet crystals) was used for the next step of changing crystal form. It is possible to obtain form I dry crystals by sufficiently drying thus obtained wet crystals.

The form I crystals (wet crystals) (7.8 g) were suspended in 216 mL of acetonitrile, and the resultant suspension was heated to 45° C. The suspension changed to a white slurry from a yellow slurry in about 1 hour. The white slurry was further stirred for 30 minutes, and then the crude product (I) (7.7 g) was added thereto. After the completion of the step of changing crystal form, the suspension was cooled to room temperature, and was then stirred at −5° C. for 30 minutes. A white solid was collected by filtration, and was then washed with acetonitrile to obtain 6.9g of form II crystals of Compound (I) (yield: 73%).

The results of powder X-ray diffraction are shown below.

Form I crystal (dry crystal): diffraction angle (2θ)=4.7, 8.0, 12.0, 12.7, and 15.9 (degree)

Form I crystal (wet crystal): diffraction angle (2θ)=4.6, 7.7, 12.7, 16.7, 19.1, and 21.1 (degree)

Form II crystal: diffraction angle (2θ)=6.0, 6.5, 12.6, 13.6, and 15.4 (degree)

EXPERIMENTAL EXAMPLE 1

Storage Stability

The form I dry crystals and the form II crystals of Compound (I) were used as samples. About 3 g of each of the samples was placed in a double polyethylene bag, and the bag containing the sample was stored in an aluminum can at 40° C. and 75% RH. After storage for 6 months, the amount of Compound (I) and the total amount of related substances of Compound (I) were measured by HPLC. As shown in Table 1, the total amount of related substances of Compound (I) was increased in the case of the form I dry crystals. On the other hand, the total amount of related substances of Compound (I) was hardly changed in the case of the form II crystals and the form II crystals are stable. Particularly, in the case of the form I crystals, the amount of an analogue B of the formula was significantly increased.

[Chemical Formula 11]

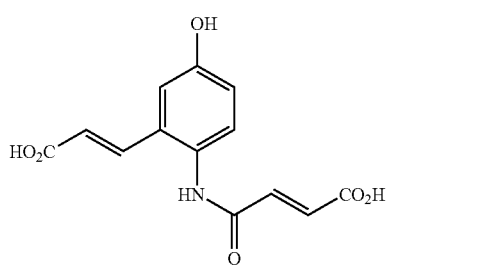

TABLE 1

| Crystal Form | | Amount of Compound (I)(%) | Amount of analogue B | Total amount of related substances(%) |
|---|---|---|---|---|
| Form I dry crystal | Initial value | 99.8% | <0.05% | 0.16% |
| | 6 months | 97.8% | 0.21% | 0.43% |
| Form II crystal | Initial value | 98.9% | <0.05% | 0.21% |
| | 6 months | 98.6% | <0.05% | 0.17% |

EXPERIMENTAL EXAMPLE 2

Stability Against Light

The form I dry crystals and the form II crystals of Compound (I) were used as samples. About 3 g of each of the samples was placed in each petri dish, and was then stored at an average temperature of 30±2° C. under light of 1,200,000 Lux·hr or 3,600,000 Lux·hr. After storage, the amount of Compound (I) and the total amount of related substances of Compound (I) were measured by HPLC. As shown in Table 2, the total amount of related substances of Compound (I) was increased in the case of the form I dry crystals. On the other hand, the total amount of related substances of Compound (I) was hardly changed in the case of the form II crystals and the form II crystals are stable against light.

TABLE 2

| Crystal Form | | Amount of Compound (I)(%) | Total amount of related substances(%) |
|---|---|---|---|
| Form I dry crystal | Initial value | 99.8% | 0.16% |
| | 1,200,000 Lux · hr | 99.2% | 0.27% |
| Form II crystal | Initial value | 100.3% | 0.15% |
| | 1,200.000 Lux · hr | 99.4% | 0.17% |
| | 3,600,000 Lux · hr | 99.3% | 0.18% |

REFERENCE EXAMPLE 1

[Chemical Formula 12]

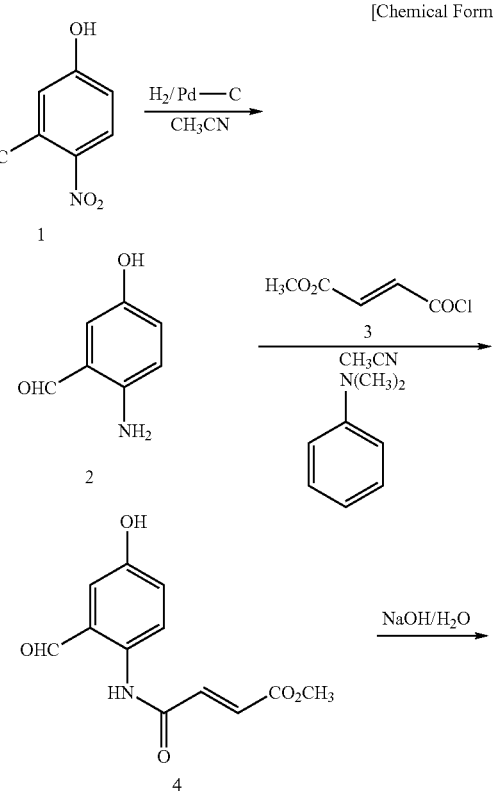

-continued

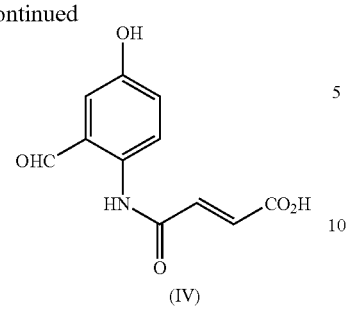

(IV)

Compound 1 (6.0 g) and 10% Pd—C (1.2 g) were suspended in acetonitrile (120 mL), and the resultant suspension was cooled to 0° C. or less. The suspension was stirred for 1 hour or longer while keeping the temperature thereof at 5° C. or lower and supplying hydrogen to the suspension. Then, Pd—C was removed by filtration, and the remaining suspension was washed with acetonitrile to obtain a solution containing Compound 2 in acetonitrile. One-third of the solution was used for the next reaction. To the solution, N,N-dimethylaniline (1.3 g) was added, and the resultant mixture was dropped into a solution containing Compound 3 (2.1 g) in acetonitrile (8 mL) cooled to –5° C. The reaction mixture was stirred for 1 hour, and then water (20 mL) was added. The mixture was heated to room temperature to obtain a solution containing Compound 4 in acetonitrile. Thus obtained solution was concentrated under reduced pressure and cooled to 0° C. Then, a 8.8% aqueous solution of sodium hydroxide (27.3 g) was dropped into the concentrated solution, and the resultant mixture was stirred for 30 minutes. Thereafter, 35% hydrochloric acid (6.1 g) was dropped into the mixture and stirred for 1 hour under ice-cooling to precipitate yellow crystals. The yellow crystals were collected by filtration, and were washed with 3.5% hydrochloric acid and water to obtain crude Compound (IV). Thus obtained crude product was dissolved in dimethylformamide (10 mL), and then 30 mL of water was dropped into the dimethylformamide solution at 45° C. to precipitate yellow Compound (IV). The solution was stirred for 30 minutes, and was further stirred for 1 hour under ice-cooling. Then, precipitated crystals were collected by filtration, and were washed with water to obtain 2.0 g of Compound (IV) (yield: 70%).

Elementary analysis (%): for $C_{11}H_9NO_5 \cdot 4H_2O$
Theoretical value: C 54.51; H 4.08; N 5.77
Analytical value: C 54.31; H 3.94; N 5.79
Moisture content (KF) (%): for $C_{11}H_9NO_5 \cdot 4H_2O$
Theoretical value: $H_2O$ 2.97
Analytical value: $H_2O$ 3.15
NMR ($d_6$-DMSO) δ: 6.66 (d, 1H, J=15.3 Hz), 7.07 (dd, 1H, J=3.0 Hz, 9.0 Hz), 7.13 (d, 1H, J=15.3 Hz), 7.19 (d, 1H, J=3.0 Hz), 7.61 (d, 1H, J=9.0 Hz)
IR ($cm^{-1}$): 3420(br), 1713, 1678, 1666, 1621, 1541, 1541, 1302, 1160

PREPARATION EXAMPLE 1

To 3.81 g of the form II crystals of Compound (I), 2.00 g of d-mannitol and 64 g of a 0.16 mol/L aqueous solution of sodium hydroxide are added to prepare a solution. To the solution, a 1 mol/L aqueous solution in sodium hydroxide is added to adjust the pH of the solution to 9.5 (the amount of the aqueous solution of sodium hydroxide is 4.79 g). An injection solvent is added to the solution so that the total amount is 80.0 g to adjust the concentration of the solution to 50.0 mg/g. The thus prepared solution is subjected to aseptic filtration, separated into fractions of 2.00 g, and freeze-dried. The thus obtained freeze-dried preparation contains 100 mg of Compound A (calculated as a 2 Na salt).

INDUSTRIAL APPLICABILITY

The form II crystals of Compound (I) of the present invention are highly stable, which makes it possible to provide high-quality pharmaceutical preparations.

The invention claimed is:
1. A crystal of a compound of the formula (I):

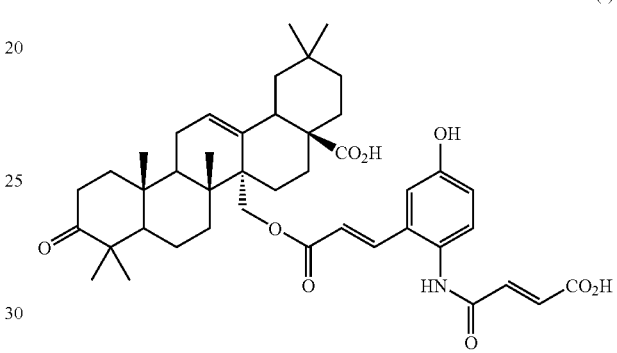

(I)

which exhibits a powder X-ray diffraction pattern having main peaks at diffraction angles (2θ) of 6.0, 6.5, 12.6, 13.6, and 15.4 (degree).

2. A method for producing the crystals as claimed in claim 1 comprising suspending or dissolving crystals of a compound of the formula (I):

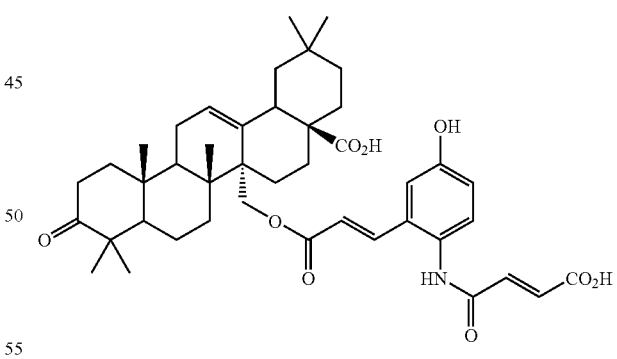

(I)

which exhibit a powder X-ray diffraction pattern having main peaks at diffraction angles (2θ) of 4.6, 7.7, 12.7, 16.7, 19.1 and 21.1 (degree) in acetonitrile to change their crystal form.

3. A method for producing a pharmaceutical preparation comprising mixing the crystals as claimed in claim 1, a solvent, and sodium hydroxide, and drying the mixture.

* * * * *